(12) United States Patent
Chang

(10) Patent No.: US 11,571,326 B2
(45) Date of Patent: *Feb. 7, 2023

(54) BIODEGRADABLE ODOR BARRIER FILM

(71) Applicant: Hollister Incorporated, Libertyville, IL (US)

(72) Inventor: Moh-Ching Oliver Chang, Lake in the Hills, IL (US)

(73) Assignee: Hollister Incorporated, Libertyville, IL (US)

( * ) Notice: Subject to any disclaimer, the term of this patent is extended or adjusted under 35 U.S.C. 154(b) by 340 days.

This patent is subject to a terminal disclaimer.

(21) Appl. No.: 16/774,705

(22) Filed: Jan. 28, 2020

(65) Prior Publication Data

US 2020/0163793 A1    May 28, 2020

Related U.S. Application Data

(63) Continuation of application No. 14/785,804, filed as application No. PCT/US2014/033674 on Apr. 10, 2014, now Pat. No. 10,583,029.

(Continued)

(51) Int. Cl.
*A61F 5/445* (2006.01)
*B32B 37/10* (2006.01)
(Continued)

(52) U.S. Cl.
CPC .............. *A61F 5/445* (2013.01); *A61F 5/448* (2013.01); *A61L 28/0015* (2013.01);
(Continued)

(58) Field of Classification Search
CPC ...... A61F 5/445; A61F 5/448; A61L 28/0015; A61L 28/0019; B32B 3/06; B32B 5/022;
(Continued)

(56) References Cited

U.S. PATENT DOCUMENTS 4,372,800 A * 2/1983 Oizumi ............... H05K 1/0366
156/332
5,009,648 A * 4/1991 Aronoff ................. B32B 27/08
604/338
(Continued)

FOREIGN PATENT DOCUMENTS

JP    H02280748 A    11/1990
JP    2001030432 A    2/2001
(Continued)

OTHER PUBLICATIONS

International Search Report issued by the ISA/US in connection with PCT/US2014/033674 dated Sep. 11, 2014.
(Continued)

*Primary Examiner* — Guy K Townsend
(74) *Attorney, Agent, or Firm* — Levenfeld Pearlstein, LLC

(57) ABSTRACT

A biodegradable odor barrier film for ostomy, continence and bowel management applications includes a barrier layer comprising at least about 90% wt. polyglycolic acid. The biodegradable odor barrier film provides excellent mechanical and odor barrier properties desired in ostomy, continence and bowel management applications.

19 Claims, 1 Drawing Sheet

Related U.S. Application Data

(60) Provisional application No. 61/824,450, filed on May 17, 2013.

(51) Int. Cl.

| | |
|---|---|
| *B32B 27/08* | (2006.01) |
| *B32B 3/28* | (2006.01) |
| *A61F 5/448* | (2006.01) |
| *B32B 27/20* | (2006.01) |
| *B32B 27/12* | (2006.01) |
| *B32B 27/36* | (2006.01) |
| *B32B 5/02* | (2006.01) |
| *B32B 27/32* | (2006.01) |
| *B32B 27/30* | (2006.01) |
| *B32B 9/02* | (2006.01) |
| *B32B 7/12* | (2006.01) |
| *B32B 3/06* | (2006.01) |
| *A61L 28/00* | (2006.01) |

(52) U.S. Cl.
CPC ............ *A61L 28/0019* (2013.01); *B32B 3/06* (2013.01); *B32B 5/022* (2013.01); *B32B 7/12* (2013.01); *B32B 9/02* (2013.01); *B32B 27/08* (2013.01); *B32B 27/12* (2013.01); *B32B 27/20* (2013.01); *B32B 27/306* (2013.01); *B32B 27/32* (2013.01); *B32B 27/36* (2013.01); *B32B 2250/40* (2013.01); *B32B 2270/00* (2013.01); *B32B 2307/7163* (2013.01); *B32B 2307/7248* (2013.01); *B32B 2307/746* (2013.01)

(58) Field of Classification Search
CPC .. B32B 7/12; B32B 9/02; B32B 27/08; B32B 27/12; B32B 27/20; B32B 27/306; B32B 27/32; B32B 27/36
See application file for complete search history.

(56) References Cited

U.S. PATENT DOCUMENTS

| | | | | |
|---|---|---|---|---|
| 5,747,212 | A * | 5/1998 | Kaplan | G03G 15/2025 399/331 |
| 5,767,168 | A * | 6/1998 | Dyer | A61L 27/10 521/64 |
| 5,853,639 | A * | 12/1998 | Kawakami | B29C 55/06 428/221 |
| 6,245,437 | B1 * | 6/2001 | Shiiki | B32B 27/304 528/425 |
| 6,258,423 | B1 | 7/2001 | Giori | |
| 6,455,161 | B1 * | 9/2002 | Regnier | C08J 5/18 428/483 |
| 7,270,860 | B2 * | 9/2007 | Giori | B32B 27/32 428/34.1 |
| 8,399,077 | B1 * | 3/2013 | Bekele | C08L 23/0853 428/35.2 |
| 8,734,411 | B2 * | 5/2014 | Shelley | A61M 1/84 604/326 |
| 10,583,029 | B2 * | 3/2020 | Chang | B32B 27/12 |
| 2005/0079372 | A1 * | 4/2005 | Schmal | B32B 27/32 428/482 |
| 2005/0118435 | A1 * | 6/2005 | DeLucia | B32B 27/283 428/447 |
| 2005/0261426 | A1 * | 11/2005 | Wood | C08F 255/02 525/66 |
| 2007/0207186 | A1 * | 9/2007 | Scanlon | B29C 55/26 623/1.42 |
| 2007/0264520 | A1 * | 11/2007 | Wood | B32B 27/302 428/606 |
| 2008/0032110 | A1 * | 2/2008 | Wood | B32B 27/28 428/401 |
| 2009/0088711 | A1 * | 4/2009 | Shelley | A61M 25/0045 604/328 |
| 2009/0151058 | A1 * | 6/2009 | Farnworth | A62B 31/00 2/457 |
| 2009/0179069 | A1 * | 7/2009 | Schmidt | B29C 48/307 229/87.08 |
| 2009/0191780 | A1 * | 7/2009 | Schiffer | C08J 5/18 442/394 |
| 2009/0216207 | A1 * | 8/2009 | Nielsen | C08J 5/18 428/220 |
| 2009/0246496 | A1 * | 10/2009 | Nielsen | C08K 5/103 428/458 |
| 2010/0032084 | A1 * | 2/2010 | Benaddi | A62D 5/00 524/425 |
| 2010/0254900 | A1 * | 10/2010 | Campbell | A61P 29/00 424/9.4 |
| 2011/0027590 | A1 * | 2/2011 | Abe | C08J 5/18 428/411.1 |
| 2011/0108185 | A1 * | 5/2011 | Hokari | B32B 27/08 156/196 |
| 2011/0120546 | A1 * | 5/2011 | Nesbitt | C09D 175/16 522/90 |
| 2012/0197237 | A1 * | 8/2012 | Holzbauer | A61M 25/0045 604/540 |
| 2013/0025764 | A1 * | 1/2013 | Henderson | C09D 5/14 156/60 |
| 2013/0143734 | A1 * | 6/2013 | Ohta | C08G 63/183 528/304 |
| 2013/0310782 | A1 * | 11/2013 | Chang | B32B 27/308 604/333 |
| 2014/0205828 | A1 * | 7/2014 | Chang | B32B 27/304 428/317.1 |
| 2014/0221951 | A1 * | 8/2014 | Chang | A61F 5/445 604/332 |
| 2015/0282978 | A1 * | 10/2015 | Henderson | A61L 31/06 604/339 |
| 2016/0058605 | A1 * | 3/2016 | Chang | B32B 27/32 604/332 |
| 2016/0225795 | A1 * | 8/2016 | Koezuka | H01L 29/78648 |
| 2016/0237329 | A1 * | 8/2016 | Takenaka | C09J 153/005 |
| 2017/0042722 | A1 * | 2/2017 | Chang | B32B 7/12 |
| 2018/0009573 | A1 * | 1/2018 | Glaser | B32B 27/08 |
| 2018/0099476 | A1 * | 4/2018 | Nakamura | A41D 13/00 |

FOREIGN PATENT DOCUMENTS

| | | |
|---|---|---|
| JP | 2003335932 A | 11/2003 |
| JP | 2005313998 A | 11/2005 |
| JP | 2008519714 A | 6/2008 |
| JP | 2008221809 A | 9/2008 |
| JP | 2009202465 A | 9/2009 |
| JP | 2010540110 A | 12/2010 |
| WO | 2011056861 A1 | 5/2011 |
| WO | 2012010361 A1 | 1/2012 |
| WO | 2012023555 A1 | 2/2012 |
| WO | 2013106361 A1 | 7/2013 |

OTHER PUBLICATIONS

JONCRYL(R) ADR-4368C Specification Sheet, pp. 1-7, 2008, BASF Corporation, Florham Park, NJ 07932; www.basf.com; http://www2.basf.us/additives/pdfs/4368C_TDS.pdf.

European Search Report issued by ISA/EPO in connection with PCT/US2014/033674 dated Jan. 2, 2017.

Extended European Search Report issued by EPO in connection with EP Patent Application No. 21215651 dated Apr. 12, 2022.

* cited by examiner

BIODEGRADABLE ODOR BARRIER FILM

CROSS-REFERENCE TO RELATED APPLICATIONS

This application is a Continuation of U.S. application Ser. No. 14/785,804, filed Oct. 20, 2015, which claims the benefit of and priority to international application No. PCT/US2014/033674, filed Apr. 10, 2014, which claims the benefit of and priority to U.S. Provisional Application No. 61/824,450, filed May 17, 2013, the contents of which are incorporated fully by reference herein.

BACKGROUND

The present disclosure relates to odor barrier films, and more particularly to biodegradable odor barrier films for medical uses such as ostomy, continence, and bowel management applications.

Gas and odor barrier films are known and widely used in the medical field. Many such films have a barrier layer that contains chlorine; other barrier layers are chlorine-free. Chlorine-containing barrier layers use, for example, copolymers of vinylidene chloride vinyl chloride (VDC-VC) copolymers) and vinylidene chloride methyl acrylate copolymer (VDC-MA copolymers). These chlorine-containing films have exceptionally high malodor-causing compound barrier properties and are typically not adversely affected by the presence of moisture. One drawback to the use of chlorine-containing compounds is that these compounds, generally, present environmental issues in disposal, for example, incineration of materials after use. Another drawback is that specialized equipment is required to process these materials due to the corrosive nature of the chlorine compounds.

Thus, barrier films including a barrier layer formed of chlorine-free vinyl alcohol based polymers, such as ethylene vinyl alcohol (EVOH) copolymers and poly(vinyl alcohol) (PVOH) were developed. However, ostomy products and other applications relating to storing and transporting bodily waste are highly demanding and typically subject materials used in such products to high levels of moisture. Further, it is extremely important that the odor barrier properties of the material are, and remain high throughout their useful life. Unfortunately, these barrier films including barrier layers formed of vinyl alcohol based polymers have been found to have reduced barrier performance in the presence of humidity.

Further, there are multilayer barrier films including a barrier layer comprising a polyamide. For example, Giori, U.S. Pat. No. 7,270,860, which is assigned to the Applicant of the present application and incorporated herein by reference, discloses a five layer film including an odor barrier layer formed from a blend of amorphous polyamide and anhydride-modified olefin polymer. WO 2011/056861, which is also assigned to the Applicant of the present application and incorporated herein by reference, also discloses a multilayer film including an odor barrier layer comprising amorphous polyamide. Such multilayer films are chlorine free, and provide improved moisture and odor barrier characteristics, tear strength, comfort and "quietness" when compared to other chlorine free films. However, although they are more environment friendly than the chlorine containing films, these barrier films are not biodegradable.

Efforts have been made to develop biodegradable ostomy, continence, and bowel management appliances. However, biodegradable films have been insufficient for providing odor barrier properties in these applications. Thus, partially biodegradable appliances, such as flushable ostomy pouch products including an inner pouch formed from a biodegradable film and an outer pouch formed of a conventional non-biodegradable barrier film, have been developed. For example, a "pouch-in-pouch" ostomy appliance includes an inner pouch made from a biodegradable film, which can be flushed in a toilet, and an outer pouch made from a conventional non-biodegradable barrier film, which provides odor barrier properties. However, such partially biodegradable appliances are more complicated to manufacture, thus, more expensive, and typically require additional steps in use, which make them less desirable to users.

Accordingly, there is a need for an odor barrier film that is biodegradable and has sufficient odor barrier and physical properties for use in ostomy, continence, and bowl management products.

BRIEF SUMMARY

Biodegradable odor barrier films and biodegradable odor barrier tubes for ostomy, continence and bowel management applications are provided according to various embodiments. Such films and tubes include a barrier layer formed essentially from polyglycolic acid (PGA) to provide excellent mechanical and odor barrier properties along with biodegradability desired in ostomy, continence, and bowel management applications.

In one aspect, a biodegradable odor barrier film for ostomy, continence and bowel management applications is provided. The biodegradable odor barrier film includes a barrier layer comprising a biodegradable resin. The barrier layer has a biodegradability that meets the requirements of ASTM D6400, EN13432 or ISO14855. Further, the biodegradable odor barrier film has a dimethyl disulfide (DMDS) breakthrough time greater than about 200 minutes when tested according to the modified Test Operations Procedure (TOP) 8-2-501 as provided in this disclosure.

In one embodiment, the barrier layer comprises polyglycolic acid (PGA) in a concentration greater than about 90 percent by weight (% wt.). For example, the barrier layer may be formed from a blend comprising about 90% wt. to about 99% wt. of PGA and a polymeric chain extender. In another example, the barrier layer may be formed of about 100% wt. PGA.

The barrier layer has a first side and a second side. In some embodiments, the biodegradable odor barrier film may include a first outer layer disposed on the first side, and a second outer layer disposed on the second side, such that the barrier layer may be sandwiched between the first and second outer layers. The first and second outer layers may also be biodegradable, such that the biodegradable odor barrier film has a biodegradability that meets the requirements of ASTM D6400, EN13432 or ISO14855.

The first and second outer layers may include a biodegradable material selected from the group consisting of starch, starch blends, polyvinyl alcohol, ethylene-vinyl alcohol copolymer, cellulose derivatives, soy protein, polycaprolactone, polylactic acid, copolyester, polyhydroxyalkanoates, and polybutylene succinate. For example, the first and second outer layers may comprise at least 70% wt. of a copolyester based on terephthalic acid, adipic acid, and 1,4-butanediol. The first and second outer layers may also include an antiblock agent, a slip agent, and/or a blowing agent.

In some embodiments, the biodegradable odor barrier film further includes first and second tie layers disposed between the barrier layer, and the first and second outer layers, respectively, in which each tie layer contacts a respective side of the barrier layer. The tie layers may be formed from a maleated polyolefin or an epoxidized polyolefin.

In another embodiment, a thickness of the barrier layer may make up about 3% to about 20% of a total thickness of the biodegradable odor barrier film. For example, a total thickness of the film may be between about 10 µm and about 1,000 µm, in which a thickness of the barrier layer may be between about 0.5 µm and about 50 µm.

A bowel management tube may be formed using any of the biodegradable odor barrier films discussed above, in which the biodegradable odor barrier film has a total thickness between about 500 µm and 1,000 µm, and the barrier layer has a thickness between about 2 µm and about 50 µm.

In another aspect, an ostomy pouch comprising a biodegradable odor barrier film is provided. The ostomy pouch includes a first side wall and a second side wall. The first and second side walls are formed from a biodegradable odor barrier film having a biodegradability that meets the requirements of ASTM D6400, EN13432 or ISO14855, and a dimethyl disulfide (DMDS) breakthrough time greater than about 200 minutes when tested according to the modified TOP 8-2-50. The ostomy pouch also includes a stoma-receiving opening on the first side wall.

In some embodiments, the first and second walls may be formed of a biodegradable odor barrier film, which includes a barrier layer comprising polyglycolic acid (PGA) in a concentration greater than about 90 percent by weight (% wt.) For example, the barrier layer may be formed from a blend comprising about 90% wt. to about 99% wt. of PGA and a polymeric chain extender. In another example, the barrier layer may be formed of about 100% wt. PGA In some embodiments, the biodegradable odor barrier film may include a first outer layer and a second outer layer disposed on each side of the barrier layer, such that the barrier layer may be sandwiched between the first and second outer layers. The first and second outer layers may also be biodegradable, such that the biodegradable odor barrier film has a biodegradability that meets the requirements of ASTM D6400, EN13432 or ISO14855. In such embodiments, the first and second outer layers may include at least 70% wt. of a copolyester based on terephthalic acid, adipic acid, and 1,4-butanediol. The first and second outer layers may also include an antiblock agent, a slip agent, and/or a blowing agent.

The ostomy pouch according to any of the embodiments discussed above may include at least one nonwoven layer attached on one or both of the first and second side walls. The nonwoven layer may also be formed from a biodegradable material.

Other aspects, objectives and advantages will become more apparent from the following detailed description when taken in conjunction with the accompanying drawings.

BRIEF DESCRIPTION OF THE DRAWINGS

The benefits and advantages of the present embodiments will become more readily apparent to those of ordinary skill in the relevant art after reviewing the following detailed description and accompanying drawings, wherein.

DETAILED DESCRIPTION

Figure 1:
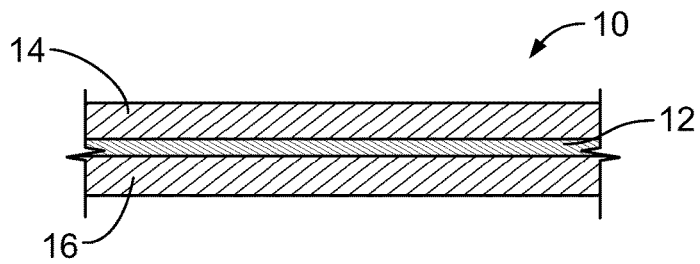
FIG. 1 is a cross-sectional illustration of a three-layer biodegradable film in accordance with an embodiment of the present disclosure.

While the present disclosure is susceptible of embodiment in various forms, there is shown in the drawings and will hereinafter be described a presently preferred embodiment with the understanding that the present disclosure is to be considered an exemplification and is not intended to limit the disclosure to the specific embodiment illustrated.

Referring now to the figures and in particular to FIG. 1, there is shown a biodegradable multilayer film 10 according to an embodiment. The film 10 may be a three-layer film including a barrier layer 12 comprising a biodegradable resin that can be composted to carbon dioxide, water and biomass under aerobic conditions in municipal and industrial aerobic composting facilities, for example, polyglycolic acid (PGA). The film 10 also may include first and second outer layers 14, 16, in which the barrier layer 12 may be sandwiched between the outer layers 14, 16.

The barrier layer 12 may be the thinnest layer of the film 10 making up less than about 20% of the total thickness, for example, between about 3% and 15% of the total thickness. The barrier layer 12 has biodegradability that satisfies the test protocols of ASTM D6400, EN13432, or ISO14855. The barrier layer 12 is also substantially impermeable to malodor causing compounds typically encountered in ostomy pouches. Such malodor causing compounds can include sulfur containing compounds and indoles. Examples of sulfur-containing compounds include dimethyl disulfide, dimethyl trisulfide, diethyl disulfide, hydrogen sulfide and methyl mercaptan. Examples of indoles, and other malodor causing compounds include 3-methyl indole and methanethiol. Other compounds will be recognized by those skilled in the art. Further, the barrier layer imparts tear strength to the film.

Polyglycolic acid (PGA) resin is particularly suitable for the barrier layer. PGA has superior oxygen, carbon dioxide, and water vapor barrier properties. Further, the inventors of the present application have discovered that PGA also has excellent odor barrier properties, which are only minimally affected by moisture content, which makes the PGA particularly suitable for ostomy, continence and bowl management applications. The PGA resin can have similar biodegradability as cellulose, and can typically degrade into carbon dioxide and water in compost within about one month.

A first outer layer 14 may be disposed on one side of the barrier layer 12, and a second outer layer 16 may be disposed on the other side of the barrier layer 12. Each of the outer layers 14, 16 may be substantially biodegradable and may comprise one or more biodegradable material that is compatible with the PGA resin in the barrier layer 12. The materials for the outer layers 14, 16 are carefully selected to provide desired film characteristics for a particular application, for example, biodegradability, water solubility, and heat sealability. Suitable biodegradable materials for the outer layers 14, 16, which are compatible with PGA resin include, but are not limited to polycaprolactone (PCL), polylactic acid (PLA), copolyester, polyhydroxyalkanoates (PHAs), and polybutylene succinate (PBS).

For ostomy pouch applications, at least one of the outer layers may be formed of a biodegradable material having good sealing characteristics, for example, heat sealability, suitable for forming a pouch, while the other outer layer may be formed of a biodegradable material, which can provide comfort against a user's skin.

In one embodiment, the barrier layer 12 is formed from a blend comprising at least 90% wt. PGA resin, for example about 99% wt. PGA resin. Each of the outer layers 14, 16 may be formed from a blend comprising a biodegradable polymeric material compatible with the PGA resin, for example, an aliphatic-aromatic copolyester resin, such as copolyester based on terephthalic acid, adipic acid, 1,4-butanediol and modular units. Such copolyester resins provide good flexibility and toughness, and are reasonably low cost, which make them suitable for ostomy, continence, and bowel management applications.

The blend for the outer layers 14, 16 may also include an antiblock agent, such as $CaCO_3$ and talc, and/or a slip agent, which can improve extrudability and reduce the risk of the outer layers 14, 16 sticking to a chill roller. Further, the blend may also include a blowing agent. In one embodiment, the barrier layer 12 and outer layers 14, 16 are coextruded.

In other embodiments, the biodegradable multilayer film can include more than three layers or less than three layers. For example, a two-layer film may include a barrier layer formed essentially of PGA resin and an outer layer formed of a biodegradable material compatible with the PGA resin. In some embodiments, a biodegradable film may be a single layer film comprising PGA resin.

Figure 2:
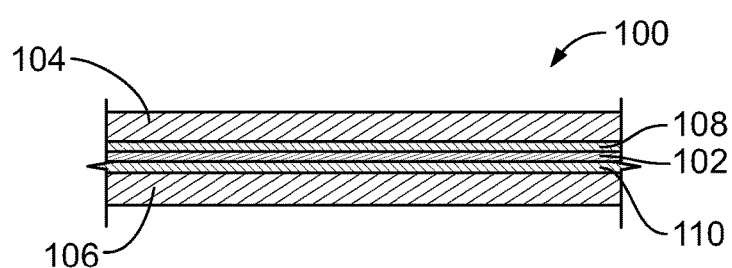
FIG. 2 is a cross-sectional illustration of a five-layer biodegradable film in accordance with another embodiment.

FIG. 2 shows another embodiment of a biodegradable multilayer film 100. The film 100 may be a five-layer film including a barrier layer 102, tie layers 108, 110, and outer layers 104, 106. Similar to the biodegradable film 10 of FIG. 1, the barrier layer 102 may be formed essentially from a biodegradable material, preferably PGA resin. The outer layers 104, 106 are also formed essentially from one or more biodegradable materials.

As shown in FIG. 2, on either side of the barrier layer 102 may be a tie layer 108, 110. Each of the tie layers 108, 110 may be formed from a material that is compatible with the PGA resin in the barrier layer 102. The tie layers 108, 110 facilitate adhesion of the barrier layer 102 to the remainder of the film structure. Outer layers 104, 106 are arranged adjacent to the tie layers 108, 110, respectively.

Suitable tie layer materials that are compatible with PGA resin include, but are not limited to, resins with maleic anhydride, such as maleated polyolefins (e.g. resins available under trade name Bynel from DuPont), or resins including epoxy functionality, such as epoxidized polyolefins (e.g. resins available under trade name Lotader® from Arkema).

In other embodiments, a biodegradable multilayer film can have various layer structures to provide desired film characteristics for ostomy, continence, or bowel management applications. For example, a biodegradable film for ostomy pouch applications may include seven layers with ABCDCBA structure, in which A represents skin/seal layers, B represents inner layers, C represents tie layers, and D represents a barrier layer formed of PGA resin. Other examples include a six-layer film including a barrier layer, two tie layers, an inner layer, and two skin layers (i.e. ABCDCA), and a five-layer film including a barrier layer, two tie layers and two outer layers (i.e. ACDCA, BCDCB or ACDCB). The biodegradable multilayer films according to various embodiments include a barrier layer formed essentially of a biodegradable material, such as PGA resin, and other layers which are substantially biodegradable.

Figure 3:
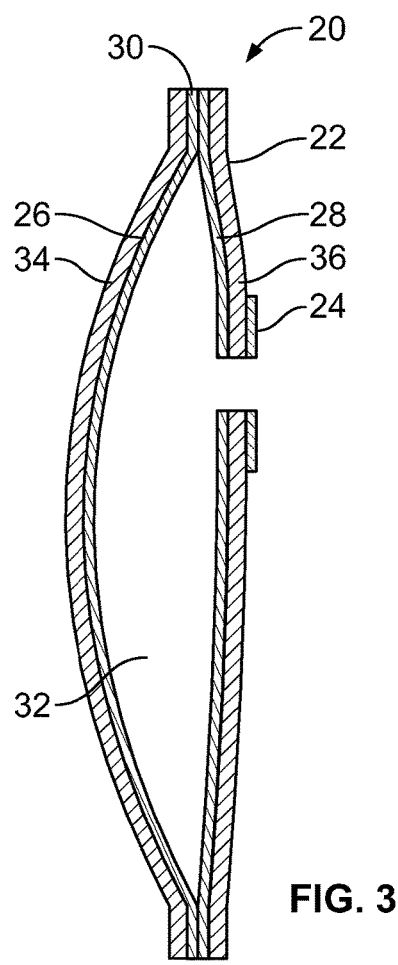
FIG. 3 is a cross-sectional illustration of an exemplary ostomy pouch including a biodegradable film.

FIG. 3 is a cross-sectional illustration of a one-piece ostomy pouch 20 made using a biodegradable odor barrier film comprising PGA resin. The ostomy pouch 20 generally includes a pouch 22 and a skin barrier 24. The pouch 22 includes first and second opposing walls 26, 28, which are sealed around peripheral edges 30 thereof to define a cavity 32 for collecting body waste. Each of the walls 26, 28 may be formed of a biodegradable odor barrier film comprising PGA resin, such as the three-layer film 10 of FIG. 1 or the five-layer film 100 of FIG. 2. The pouch 22 also includes a first nonwoven layer 34 attached to the first wall 26, and a second nonwoven layer 36 attached to the second wall 28. The nonwoven layers 34, 36 are attached to the respective walls 26, 28 via heat sealing or an adhesive. The nonwoven layers 34, 36 may be formed from one or more biodegradable materials, and thus, substantially biodegradable. In other embodiments, the ostomy pouch 20 may not include a nonwoven layer or include only one nonwoven layer.

Figure 4:
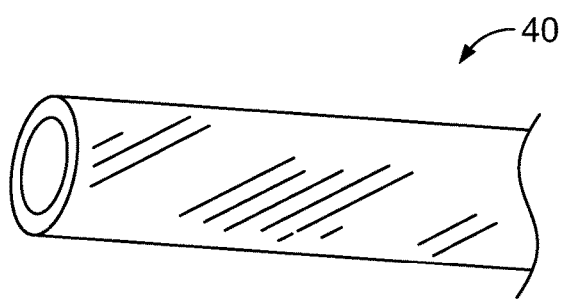
FIG. 4 is an illustration of an exemplary bowel management tube made from a biodegradable material.

FIG. 4 is a bowel management tube 40 comprising a biodegradable odor barrier layer comprising PGA resin. The bowel management tube 40 can be made using a biodegradable odor barrier film according to various embodiments in the present disclosure. For example, the bowel management tube 40 can be made using the three-layer film 10 of FIG. 1, or the five-layer film 100 of FIG. 2. In other embodiments, the bowel management tube 40 can be extruded as a single layer tube comprising PGA resin. Further, the bowel management tube 40 may be coextruded as a multilayer tubing including an odor barrier layer comprising PGA resin, and inner and outer layers comprising a biodegradable material similar to the above described biodegradable film embodiments.

Sample Multilayer Biodegradable Films

Four different three-layer film samples including a barrier layer formed essentially from PGA resin were prepared. Each of the film samples includes a barrier layer and two outer layers as shown in FIG. 1.

Sample 303-2 had a total thickness of about 43 μm. The barrier layer 12 had a thickness of about 4 μm and comprised about 99% wt. of PGA (Kuredux® PGA B35 from Kureha) and about 1% wt. of an oligomeric chain extender based on multiple epoxy functional groups (Joncryl® ADR 4368 from BASF). Each of the outer layers 14, 16 had a thickness of about 19.5 μm and was formed from a blend comprising biodegradable polymeric materials. The blend included about 78.5% wt. of Ecoflex® F Blend C1200 from BASF (copolyester based on terephthalic acid, adipic acid, and 1, 4-butanediol), about 20% wt. of Ecoflex® Batch AB1 from BASF (antiblock agent masterbatch including about 60% wt. of fine chalk and about 40% wt. of Ecotlex® F Blend C1200), and about 1.5% wt. of Ecoflex® Batch SL1 from BASF (slip agent masterbatch including about 10% wt. of erucamide and about 90% wt. of Ecoflex® F Blend C1200.)

Sample 303-3 had a total thickness of about 69 μm. The barrier layer 12 had a thickness of about 4 μm and comprised about 99% wt. of PGA (Kuredux® PGA B35 from Kureha) and about 1% wt. of an oligomeric chain extender based on multiple epoxy functional groups (Joncryl® ADR 4368 from BASF). Each of the outer layers 14, 16 had a thickness of about 32.5 μm and was formed of the same blend used for the outer layers of Sample 303-2.

Sample 303-4 had a total thickness of about 56 μm. The barrier layer 12 had a thickness of about 6 μm and comprised about 99% wt. of PGA (Kuredux® PGA B35 from Kureha) and about 1% wt. of an oligomeric chain extender based on multiple epoxy functional groups (Joncryl® ADR 4368 from BASF). Each of the outer layers 14, 16 had a thickness of about 25 μm and was formed of the same blend used for the outer layers of Sample 303-2.

Sample 303-5 had a total thickness of about 58 μm. The barrier layer 12 had a thickness of about 3 μm and comprised about 99% wt. of PGA (Kuredux® PGA B35 from Kureha) and about 1% wt. of an oligomeric chain extender based on multiple epoxy functional groups (Joncryl® ADR 4368 from BASF). Each of the outer layers 14, 16 had a thickness of about 27.5 μm and was formed of the same blend used for the outer layers of Sample 303-2. The sample films are summarized in Table 1

TABLE 1

Sample Biodegradable Odor Barrier Films

| Sample Number | Outer Layer | Barrier Layer | Outer Layer |
|---|---|---|---|
| 303-2 (43 μm) | 78.5% wt. Ecoflex ® F Blend C1200 + 20% wt. Ecoflex ® Batch AB1 + 1.5% wt. Ecoflex ® Batch SL1 (19.5 μm) | 99% wt. Kuredux ® PGA B35 + 1% wt. Joncryl ® ADR 4368 (4 μm) | 78.5% wt. Ecoflex ® F Blend C1200 + 20% wt. Ecoflex ® Batch AB1 + 1.5% wt. Ecoflex ® Batch SL1 (19.5 μm) |
| 303-3 (69 μm) | 78.5% wt. Ecoflex ® F Blend C1200 + 20% wt. Ecoflex ® Batch AB1 + 1.5% wt. Ecoflex ® Batch SL1 (32.5 μm) | 99% wt. Kuredux ® PGA B35 + 1% wt. Joncryl ® ADR 4368 (4 μm) | 78.5% wt. Ecoflex ® F Blend C1200 + 20% wt. Ecoflex ® Batch AB1 + 1.5% wt. Ecoflex ® Batch SL1 (32.5 μm) |
| 303-4 (56 μm) | 78.5% wt. Ecoflex ® F Blend C1200 + 20% wt. Ecoflex ® Batch AB1 + 1.5% wt. Ecoflex ® Batch SL1 (25 μm) | 99% wt. Kuredux ® PGA B35 + 1% wt. Joncryl ® ADR 4368 (6 μm) | 78.5% wt. Ecoflex ® F Blend C1200 + 20% wt. Ecoflex ® Batch AB1 + 1.5% wt. Ecoflex ® Batch SL1 (25 μm) |
| 303-5 (58 μm) | 78.5% wt. Ecoflex ® F Blend C1200 + 20% wt. Ecoflex ® Batch AB1 + 1.5% wt. Ecoflex ® Batch SL1 (27.5 μm) | 99% wt. Kuredux ® PGA B35 + 1% wt. Joncryl ® ADR 4368 (3 μm) | 78.5% wt. Ecoflex ® F Blend C1200 + 20% wt. Ecoflex ® Batch AB1 + 1.5% wt. Ecoflex ® Batch SL1 (27.5 μm) |

The film samples and a control film sample were tested for tensile properties in both the machine direction (MD) and the transverse direction (TD). The control film sample was measured using gas chromatography (GC). The test results of the samples and control film are summarized in Table 2, below.

TABLE 2

Tensile and Odor Barrier Test Results

| | Sample 303-2 | Sample 303-3 | Sample 303-4 | Sample 303-5 | Control |
|---|---|---|---|---|---|
| Total Film Thickness (μm) | 43 | 69 | 56 | 58 | 76 |
| Barrier Layer Thickness (μm) | 4 | 4 | 6 | 3 | 5 |
| Machine Direction (MD) Tensile Properties | | | | | |
| Tensile Strength (psi) | 3753 | 3726 | 4156 | 3655 | 2543 |
| Elongation at Break (%) | 476 | 481 | 518 | 504 | 568 |
| Modulus (1,000 psi) | 93.7 | 89.5 | 76.6 | 87.3 | 23.3 |
| Transverse Direction (TD) Tensile Properties | | | | | |
| Tensile Strength (psi) | 3230 | 2898 | 2946 | 2058 | 1705 |
| Elongation at Break (%) | 457 | 505 | 391 | 267 | 761 |
| Modulus (1,000 psi) | 110.5 | 102.4 | 110.0 | 68.7 | 24.8 |
| Gas Chromatography (GC) Odor Testing (Modified TOP 8-2-501) | | | | | |
| Dimethyl Disulfide (DMDS) Breakthrough Time (minutes) | >1440 | >1440 | >1440 | >1440 | 141 | prepared using a multilayer odor barrier film, which is commercially used in some ostomy pouches. The control film sample had a total thickness of about 76 μm, and included an odor barrier layer having a thickness of about 5 μm and comprising vinylidene chloride-methyl acrylate copolymer.

The samples were also tested for odor barrier properties. Following a modified version of Test Operations Procedure (TOP) 8-2-501 for Permeation and Penetration of Air-Permeable, Semi-permeable, and Impermeable Materials with Chemical Agents or Simulants, a time for dimethyl disulfide (DMDS) to permeate through a film sample was measured. In this test, 15% wt. DMDS in isopropyl myristate solvent was used as a challenging gas with nitrogen carrier gas. The flow rate of the carrier gas across a sample film was 125 cc/min and the temperature in the test chamber was 38±2° C. A breakthrough time, which is a time for the DMDS challenging gas to permeate through a sample film and reach 1 part per million (ppm) concentration, was As shown in Table 2, the sample biodegradable films including a barrier layer comprising PGA provided significantly improved odor barrier properties when compared to the control film sample. Further, the sample biodegradable films also had better or comparable tensile properties as the control film sample. Thus, the sample biodegradable films can be used to make durable ostomy appliances having excellent odor barrier properties.

In the present disclosure, all percentages of constituents are by weight, unless otherwise indicated. In the present disclosure, the words "a" or "an" are to be taken to include both the singular and the plural. Conversely, any reference to plural items shall, where appropriate, include the singular. All of the concentrations noted herein as percentage are percent by weight unless otherwise noted.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. A biodegradable odor barrier film for ostomy, continence and bowel management applications, comprising:
   a barrier layer comprising polyglycolic acid (PGA), the barrier layer having a biodegradability that meets the requirements of ASTM D6400, EN13432 or ISO14855;
   an outer layer comprising a copolyester based on terephthalic acid, adipic acid, and 1,4-butanediol, wherein the copolyester is an aliphatic-aromatic copolyester that is biodegradable to terephthalic acid, adipic acid, and 1,4-butanediol and meets the requirements of ASTM D6400, EN13432, and
   wherein the biodegradable odor barrier film has a biodegradability that meets the requirements of ASTM D6400, EN13432 or ISO14855 and a dimethyl disulfide (DMDS) breakthrough time greater than about 200 minutes when tested according to the modified Test Operations Procedure (TOP) 8-2-501.

2. The film of claim 1, wherein the barrier layer comprises polyglycolic acid (PGA) in a concentration greater than about 90 percent by weight (% wt.).

3. The film of claim 1, wherein the barrier layer is formed from a blend comprising about 90% wt. to about 99.9% wt. of PGA and a polymeric chain extender.

4. The film of claim 1, wherein the barrier layer is formed of about 100% wt. PGA.

5. The film claim 1, wherein the barrier layer has a first side and a second side, wherein a first outer layer is disposed on the first side and a second outer layer is disposed on the second side, such that the barrier layer is sandwiched between the first and second outer layers, wherein the first and second outer layers are biodegradable.

6. The film of claim 5, wherein the first and second outer layers include a biodegradable material selected from the group consisting of starch, starch blends, polyvinyl alcohol, ethylene-vinyl alcohol copolymer, cellulose derivatives, soy protein, polycaprolactone, polylactic acid, copolyester, polyhydroxyalkanoates, and polybutylene succinate.

7. The film of claim 5, wherein the first and second outer layers comprise at least 70% wt. of a copolyester based on terephthalic acid, adipic acid, and 1,4-butanediol.

8. The film of claim 6, wherein the first and second outer layers further comprises an antiblock agent, a slip agent, and/or a blowing agent.

9. The film of claim 5, further comprising first and second tie layers disposed between the barrier layer and the first and second outer layers, respectively, the tie layers formed from a maleated polyolefin or an epoxidized polyolefin, wherein each tie layer contacting a respective side of the barrier layer.

10. The film of claim 5, wherein a thickness of the barrier layer makes up about 3% to 20% of a total thickness of the film.

11. The film of claim 5, wherein a total thickness of the film is between about 10 µm and about 1,000 µm, and a thickness of the barrier layer is between about 0.5 µm and about 50 µm.

12. A bowel management tube formed of the film of claim 1, wherein the film has a total thickness between about 500 µm and 1,000 µm, and the barrier layer has a thickness between about 2 µm and about 50 µm.

13. An ostomy pouch comprising:
    a first side wall and a second side wall, wherein the first and second side walls are formed from the film of claim 1; and
    a stoma-receiving opening on the first side wall.

14. The ostomy pouch of claim 13, wherein the biodegradable odor barrier film includes a barrier layer comprising polyglycolic acid (PGA) in a concentration greater than about 90 percent by weight (% wt.).

15. The ostomy pouch of claim 14, wherein the barrier layer is formed from a blend comprising about 90% wt. to about 99% wt. of PGA and a polymeric chain extender.

16. The ostomy pouch of claim 13, wherein the barrier layer has a first side and a second side, wherein a first outer layer is disposed on the first side and a second outer layer is disposed on the second side, such that the barrier layer is sandwiched between the first and second outer layers, wherein the first and second outer layers are biodegradable, and the film has a biodegradability that meets the requirements of ASTM D6400, EN13432 or ISO14855.

17. The ostomy pouch of claim 16, wherein the first and second outer layers comprise at least 70% wt. of a copolyester based on terephthalic acid, adipic acid, and 1,4-butanediol.

18. The ostomy pouch of claim 17, wherein the first and second outer layers further comprises an antiblock agent, a slip agent, and/or a blowing agent.

19. The ostomy pouch of claim 13, further including at least one nonwoven layer attached on one or both of the first and second side walls, wherein the nonwoven layer is formed from a biodegradable material.

* * * * *